(12) United States Patent
Barwell et al.

(10) Patent No.: US 12,642,462 B2
(45) Date of Patent: Jun. 2, 2026

(54) ANALYTE SENSOR COMPONENT

(71) Applicant: SciLogica Corp., Denver, CO (US)

(72) Inventors: Nicholas Paul Barwell, Warwickshire (GB); Barry Colin Crane, Oxon (GB); Alasdair Allan Mackenzie, Herefordshires (GB)

(73) Assignee: SciLogica Corp., Denver, CO (US)

( * ) Notice: Subject to any disclaimer, the term of this patent is extended or adjusted under 35 U.S.C. 154(b) by 10 days.

(21) Appl. No.: 18/473,053

(22) Filed: Sep. 22, 2023

(65) Prior Publication Data

US 2024/0008776 A1 Jan. 11, 2024

Related U.S. Application Data

(63) Continuation of application No. 17/174,263, filed on Feb. 11, 2021, now abandoned.

(51) Int. Cl.
*A61B 5/1455* (2006.01)
*A61B 5/145* (2006.01)
*A61B 5/1459* (2006.01)

(52) U.S. Cl.
CPC ........ *A61B 5/1459* (2013.01); *A61B 5/14546* (2013.01); *A61B 2560/0223* (2013.01); *A61B 2562/0271* (2013.01)

(58) Field of Classification Search
CPC .. A61B 5/1455; A61B 5/1459; A61B 5/14546
See application file for complete search history.

(56) References Cited

U.S. PATENT DOCUMENTS 5,601,080 A 2/1997 Oppenheimer
6,009,339 A 12/1999 Bentsen et al.
(Continued)

FOREIGN PATENT DOCUMENTS

CN 101231248 B 12/2010
EP 0994669 A1 4/2000
JP 2001/513676 A 9/2001

OTHER PUBLICATIONS

Chu et al., "Review on Recent Developments of Fluorescent Oxygen and Carbon Dioxide Optical Fiber Sensors", Photonic Sensors (2011).
(Continued)

*Primary Examiner* — Marjan Fardanesh
(74) *Attorney, Agent, or Firm* — Harness, Dickey & Pierce, P.L.C.

(57) ABSTRACT

A sensor component for use in a system for measuring concentration of analytes in fluid in a fluid line comprises one or more sensing elements having an optical property that varies with the concentration of the analytes and engages with the fluid line such that the sensing elements are exposed to the fluid. The sensor component comprises a connector connecting to one or more optical waveguides and transmits light between the waveguides and the sensing elements. The sensor component comprises one or more of a sampling port configured to provide fluidic access to the fluid line, a data storage medium storing data representing information about the sensor component, and a reflective element. Where it comprises a reflective element, the sensor component transmits light between the waveguides and the reflective element on a separate optical path from an optical path between the waveguides and the sensing elements.

17 Claims, 5 Drawing Sheets

(56) References Cited

U.S. PATENT DOCUMENTS

| | | | |
|---|---|---|---|
| 6,101,406 A * | 8/2000 | Hacker .............. | A61M 1/3621 |
| | | | 422/68.1 |
| 2016/0058934 A1 | 3/2016 | Strohhofer et al. | |

OTHER PUBLICATIONS

Ge et al., "High-stability non-invasive autoclavable naked optical CO2 sensor", Biosensors and Bioelectronics 18 (2003).
Molecular Probes Handbook Chapter 20, ThermoFisher Scientific.
European Search Report regarding Application No. 21188424.2-1113 dated Apr. 21, 2022.
International Search Report and Written Opinion regarding Applicaiton No. PCT/GB2022/050354 dated Apr. 21, 2022.
Japanese Office Action regarding Application No. 2023-547249, dated Aug. 26, 2025.

* cited by examiner

ANALYTE SENSOR COMPONENT

CROSS-REFERENCE TO RELATED APPLICATION

This application is a continuation of U.S. patent application Ser. No. 17/174,263 filed on Feb. 11, 2021, the entire disclosure of which is incorporated herein by reference.

FIELD

The present invention relates to sensor components used to measure the concentration of analytes in a fluid, specifically using an optical property of a sensing element.

BACKGROUND

It is desirable in many areas to be able to determine the concentration of an analyte in a fluid which may contain a mixture of several different substances. For example, in clinical settings it is important to be able to accurately determine the concentration of oxygen in a patient's blood in real time to detect and prevent hypoxia. Examples of clinical settings where monitoring of blood analytes is important include cardiopulmonary Bypass (CPB), extracorporeal membrane oxygenation (ECMO), and continuous renal replacement therapies (CRRT).

CPB technology allows cardiac surgical procedures to be performed in a motionless bloodless surgical field. Modern CPB machines have systems for monitoring pressures, temperature, oxygen saturation, haemoglobin as well as bubble detectors and reservoir low level detection alarms. Cardiopulmonary bypass patients are subject to physiological variations in in their blood gas levels due to oxygenation, electrolyte changes, and fluid shifts that occur during CPB. Potential adverse patient outcomes due to these variations may include hypoxia and hyperoxia, hypocapnia and hypercapnia, and acid base alterations. The American Society of Extracorporeal Technology-Standards and Guidelines for Perfusion Practice, Appendix D, May 2017, proposes that PO2, PCO2, pH, SO2, potassium, ionised calcium, sodium, lactate, glucose, and haemoglobin/haematocrit be measured frequently or continuously. Other useful parameters can be calculated from these measured blood gas data—base excess, bicarbonate, oxygen delivery, oxygen consumption and oxygen extraction ratio.

ECMO has more recently evolved from CPB and is applicable to patients who are hypoxaemic despite maximal conventional ventilatory support, who have significant ventilator-induced lung injury, or who are in cardiogenic shock. The equipment set up is similar to that of CPB but is generally used for very long periods of time (e.g., 30 days is not uncommon) and usually resides within the Intensive Care Unit. CRRT are hemodialysis treatments that are provided as a continuous 24 hour per day therapy and is appropriate for patients suffering acute renal failure (ARF) that are hemodynamically unstable. Intermittent hemodialysis is appropriate for patients that have chronic renal impairment.

One known type of sensor employed in these settings uses a luminescent compound, for example a fluorescent organic dye, with a luminescence lifetime which depends on the concentration of the analyte. By exciting the luminescent compound and measuring its luminescence lifetime, the concentration of the analyte can be determined. This type of system has the advantage that it can be operated continuously, so does not require taking regular samples, for example of blood, for analysis or other similarly inconvenient procedures. The clinical utility of continuous real time monitoring is particularly important when monitoring clinically critical, rapidly changing analytes in seriously ill patients. The information provided enables the clinician to respond by titrating administered therapies. Thus, continuous real time data can be considered as providing feedback to therapy.

With intermittent testing a clinician's view of the status of the patient at a point where a new blood sample is to be taken is governed by the analyte value given by the previous sample. Gaps in the knowledge of a patient's status between blood samples (known as blind intervals) can be a risk to the patient. These gaps can be eliminated by using a continuous sensor. Continuous monitoring should be able to provide accurate measurement of a given analyte over prolonged periods of time, provide direction to the movement of analyte concentration (indicating trending) and in doing so provide continuous, minute by minute, patient status information to the clinician. This aids the provision of effective therapy and eliminates blind intervals, thereby reducing risk to the patient.

SUMMARY

To provide these benefits an important requirement for a continuous sensor is to maintain accuracy over prolonged periods of time. Inaccuracies can be due to continuous drift of the sensor reading or more sudden changes, for example due to damage to the sensor. These inaccuracies are of critical importance since they may not be readily differentiated from true physiological changes in the concentration of the analyte. Hence, the clinician may be provided with erroneous information that incorrectly influences the administered therapy, thereby putting the patient at risk. This is less of a concern for intermittent monitoring, where a blood sample is taken and introduced to a sensor such as a blood gas analyser. This is because the sensor is calibrated just prior to each measurement, so although the sensor is likely to drift relatively quickly, it is of no consequence in terms of accuracy since there is little time to drift between calibration and measurement.

The first aspect of the present invention is concerned with providing a sensor component for continuous monitoring that is more accurate and less prone to drift.

According to a first aspect of the invention, there is provided a sensor component for use in a system for measuring the concentration of one or more analytes in fluid in a fluid line, the sensor component comprising one or more sensing elements having an optical property that varies with the concentration of the one or more analytes in the fluid, the sensor component being configured to engage with the fluid line such that the sensing elements are exposed to the fluid in the fluid line, a connector configured to connect to one or more optical waveguides, the sensor component being configured to transmit light between the one or more optical waveguides and the one or more sensing elements, and a sampling port configured to provide fluidic access to the fluid line when the sensor component is engaged with the fluid line.

The sampling port provided as part of the sensor component means that, either during initial setup of the sensor component or if it has been ascertained that readings from one or more of the sensing elements do drift, leading to inaccuracy over a period of time, then a sample of the fluid can be taken from the local port. The sample can be analysed by an approved analyser and the value used to adjust the readings from the sensing elements to compensate for the inaccuracy. Including the sampling port as part of the sensor component also has the advantage that fluid samples will be taken in physical proximity to the sensing elements, such that the concentration of analyte in the fluid sample will reflect the concentration at the sensing elements as accurately as possible.

In some embodiments, the sampling port comprises a one-way valve configured to permit one-way fluid flow out of the fluid line. Using a one-way valve prevents the sampling port being used to introduce substances into the fluid line, which may not be appropriate at the location of the sensor component or may cause erroneous readings from the sensor component by locally affecting the concentration of an analyte.

In some embodiments, the sampling port comprises a component fitting configured to engage with an external fitting. Using a component fitting allows the sampling port to be reliably and securely engaged by an external fitting on a device used to take samples. This can prevent possible contamination or other errors during sampling. In some embodiments, the component fitting comprises a Luer fitting. This is a commonly available type of fitting in clinical settings.

In some embodiments, the sampling port is configured to open upon engagement of the external fitting with the component fitting. This reduces the number of operations required to acquire a sample, thereby improving ease of use.

In some embodiments, the sampling port is self-closing. This also improves ease of use by reducing the operations required by a user and reduces the chance of contamination if the sampling port is not promptly and correctly closed after taking a sample.

In some embodiments, the sampling port is at most 20 cm from the one or more sensing elements. Physical proximity to the sensing elements ensures that the sample taken using the sampling port has analyte concentrations indicative of those at the sensing elements at the time of sampling. This helps to improve the accuracy of calibration performed using the sample.

In some embodiments, the sampling port comprises a removable cap configured to seal the sampling port. This allows the port to be more securely sealed and protected from possible damage, particularly during extended periods of non-use.

A second aspect of the present invention is also concerned with providing a sensor component for continuous monitoring that is more accurate and less prone to drift.

According to the second aspect of the invention, there is provided a sensor component for use in a system for measuring the concentration of one or more analytes in fluid in a fluid line, the sensor component comprising one or more sensing elements having an optical property that varies with the concentration of the one or more analytes in the fluid, the sensor component being configured to engage with the fluid line such that the sensing elements are exposed to the fluid in the fluid line when the sensor component is engaged with the fluid line, a connector configured to connect to one or more optical waveguides, the sensor component being configured to transmit light between the one or more optical waveguides and the one or more sensing elements, a reflective element, the sensor component being configured also to transmit the light between the one or more optical waveguides and the reflective element on a separate optical path from an optical path between the one or more optical waveguides and the one or more sensing elements.

Providing the reflective element allows for light to be transmitted along an optical path that does not contain the sensing elements. This provides an additional measurement that can be compared to the measurements obtained from optical paths that do contain the sensing elements. In turn, such comparison ensures that any inaccuracies generated by factors such as small mechanical shifts in optical interfaces or the generation of light losses through minor damage to the one or more optical waveguides can be distinguished from changes in transmission that are due to changes in the concentrations of analytes in the fluid. This allows an assessment of whether the accuracy of the measurements of analyte concentration are likely to have deteriorated far enough that remedial action, such as recalibration or replacement of the sensor component, are necessary.

In some embodiments, the reflective element is concave. A concave reflector can concentrate light and cause it to be transmitted more effectively back to the optical waveguide after reflection.

In some embodiments, the reflective element is planar. A planar reflective element may be more straightforward to manufacture and assemble than a concave reflector.

In some embodiments, the reflective element is configured to reflect at least 10% of light incident thereon back to the one or more waveguides. This provides a minimum level of reflectivity such that signal from the reflective element can reliably be detected.

Another important requirement for sensor components, particularly where they are replaceable or disposable, is that individual sensor components and associated information are not confused with one another. Sensor components may have properties that vary between batches, may be associated with particular equipment or patients, and have various other associated metadata. Keeping track of such information is important to provide accurate information and ensure patient safety but may also be difficult where multiple individual sensor components are stored or in use in the same environment.

A third aspect of the present invention is concerned with providing a replaceable sensor component for continuous monitoring that is accurate, and which allows information to be easily and robustly associated with the sensor component.

According to the third aspect of the invention, there is provided a replaceable sensor component for use in a system for measuring the concentration of one or more analytes in fluid in a fluid line, the sensor component comprising one or more sensing elements having an optical property that varies with the concentration of the one or more analytes in the fluid, the sensor component being configured to engage with the fluid line such that the sensing elements are exposed to the fluid in the fluid line when the sensor component is engaged with the fluid line, a connector configured to connect to one or more optical waveguides, the sensor component being configured to transmit light between the one or more optical waveguides and the one or more sensing elements, and a data storage medium configured to store data representing information about the sensor component.

Storing information about the sensor component on a data storage medium is advantageous when the sensor component is replaceable, e.g. disposable and/or single use. This ensures that information about parameters specific to each sensor component is intrinsically linked to the particular sensor component, thereby reducing the likelihood of errors caused by confusion between different sensor components.

In some embodiments, the replaceable sensor component further comprises an interface circuit configured to transmit signals between the data storage medium and the system. This can simplify the retrieval or storage of information in the data storage medium. In some embodiments, the interface circuit is configured to transmit the signals wirelessly. This can improve ease of use by eliminating the need for physical connection to the data storage medium.

In some embodiments, the information comprises one or more characteristics of the one or more sensing elements. The characteristics of the sensing elements may vary between manufacturing batches, so storing their characteristics on the data storage medium ensures accurate characteristics for each sensor component are easily available.

In some embodiments, the information comprises calibration information about the variation of the optical property of the sensing elements with one or both of the concentration of the one or more analytes and the temperature of the sensing elements. In this case, storing the information on the data storage medium of the sensor component improves the accuracy of determinations of the concentration of the analytes by ensuring calibration information specific to each sensor component is available.

In some embodiments, the information comprises one or more characteristics of a calibration fluid used for calibration of the replaceable sensor component. This simplifies the calibration process when particular calibration fluids are used as characteristics do not have to be provided by the user. In some embodiments, the information comprises a variation of the pH of the calibration fluid with temperature. This allows the accuracy of calibration to be further improved depending on the conditions at the time of calibration.

In some embodiments, the information comprises an identifier of a patient with whom the replaceable sensor component is associated. This can prevent the sensor component being reused with multiple patients, that could lead to cross-contamination or other problems. In some embodiments, the data storage medium is configured to receive the identifier during initialisation of the system and store the identifier such that the replaceable sensor component is permanently associated with the patient. Permanently storing the patient identifier further helps to prevent reuse of the sensor component with multiple patients.

In some embodiments, the information comprises an identifier of the system with which the replaceable sensor component is associated. The behaviour or performance of the sensor component may vary depending on the system to which it is connected, and so reusing a sensor component with a different system may cause calibration to become inaccurate. Storing a system identifier can help to prevent or identify when this occurs.

In some embodiments, the information comprises one or more of an indication of prior use of the replaceable sensor component, an indication of whether damage has occurred to the replaceable sensor component, a use-by date after which the replaceable sensor component should not be used, an in-use lifetime of the replaceable sensor component, a length of time for which the replaceable sensor component has been used, a unique identifier of the replaceable sensor component, a date of manufacture of the replaceable sensor component, a time at which the replaceable sensor component was last calibrated, and an indication of the number and/or type of errors that have occurred during use of the replaceable sensor component. All of these parameters can be used to assess the validity of the calibration of the sensor component, and whether its continued use is advisable, thereby improving the accuracy of readings obtained and patient safety. Knowledge of some of these parameters may also be required for regulatory compliance, and so storing them on the sensor component itself reduces the burden on the user of recording the information elsewhere.

The following additional features may be combined with any of the three aspects of the invention discussed above.

In some embodiments, the sensor component further comprises a fluid-permeable support element for supporting the sensing elements arranged to be between the sensing elements and the fluid in the fluid line when the sensor component is engaged with the fluid line. This can protect the sensing elements from mechanical effects due to, for example, pulsatile flow of fluid through the fluid line, that could affect their position and thereby the measurements of their optical property. In some embodiments, the permeable support element comprises a mesh. This is a particularly straightforward way of providing a fluid-permeable support element that is easy to manufacture and assemble.

In some embodiments, the sensing elements comprise a membrane permeable to at least one of the analytes configured to be exposed to the fluid in the fluid line when the sensor component is engaged with the fluid line. This can provide analyte-specific permeability such that each sensing element is not exposed to other components of the fluid that may affect its interaction with the target analyte.

In some embodiments, the sensor component comprises two or more sensing elements. This allows sensing of multiple analytes simultaneously in a single sensor component, thereby reducing the number of components required to monitor the concentration of analytes in the fluid.

In some embodiments, the sensor component further comprises a light-absorbing element positioned between the sensing elements. This prevents cross stimulation of sensing elements due to light directed to other sensing elements, thereby reducing possible sources of error.

In some embodiments, the connector comprises a transparent optical element in respect of the or each sensing element configured to transfer light between the sensing element and the one or more optical waveguides. This can protect the sensing elements from mechanical or chemical damage when the sensor component is not connected to the one or more optical waveguides. In some embodiments, the transparent optical element comprises a waveguide. This reduces light loss through the transparent optical component.

In some embodiments, the sensor component further comprises a temperature sensor arranged to sense the temperature of the one or more sensing elements. This can allow for adjustment of measurements to account for changes in the optical property or its dependence on the concentration of the analyte as a function of temperature. In some embodiments, the temperature-sensitive element is a thermistor or a thermocouple. These are readily available and well-understood components for measuring temperature.

In some embodiments, the sensor component is configured to engage with a wall of the fluid line. This provides a convenient engagement mechanism and minimises the size of the sensor component.

In some embodiments, the sensor component further comprises a conduit, the sensing elements being exposed to fluid in the conduit and the conduit is configured to be inserted into the fluid line for engagement of the sensor component with the fluid line. This may be more convenient in some situations according to the configuration of the fluid line with which the sensor component engages.

In some embodiments, the conduit is configured to be inserted into the fluid line in an in-line configuration. This minimises disruption to the flow of fluid in the fluid line.

In some embodiments, the conduit is configured to be inserted into the fluid line in a shunt configuration. This allows the sensor component to be attached and removed without interrupting the flow of fluid in the fluid line.

BRIEF DESCRIPTION OF DRAWINGS

Embodiments of the present invention will now be described by way of non-limitative example with reference to the accompanying drawings, in which.

DETAILED DESCRIPTION

As mentioned above, the present invention has three aspects, which all relate to improving the accuracy of measurements using the sensor component, and aiding in detecting and reducing drift in the measurements when the sensor component is used continuously for extended periods of use. The features that differ between the three aspects are respectively the sampling port, the reflective element, and the data storage medium. Each of these features will be discussed in further detail below. In the embodiments discussed herein, all three of these features are provided simultaneously in the same sensor component. This provides the maximum benefit from the combination of all of the features. However, it should be understood that it is not necessary to provide these three features in combination, and that it would equally be possible to provide a sensor component with any one of the three features in isolation, as represented by the three aspects mentioned above. It would also be possible to provide a sensor component having any combination of two of the three features, and doing so would still provide corresponding benefits and advantages.

Figure 1:
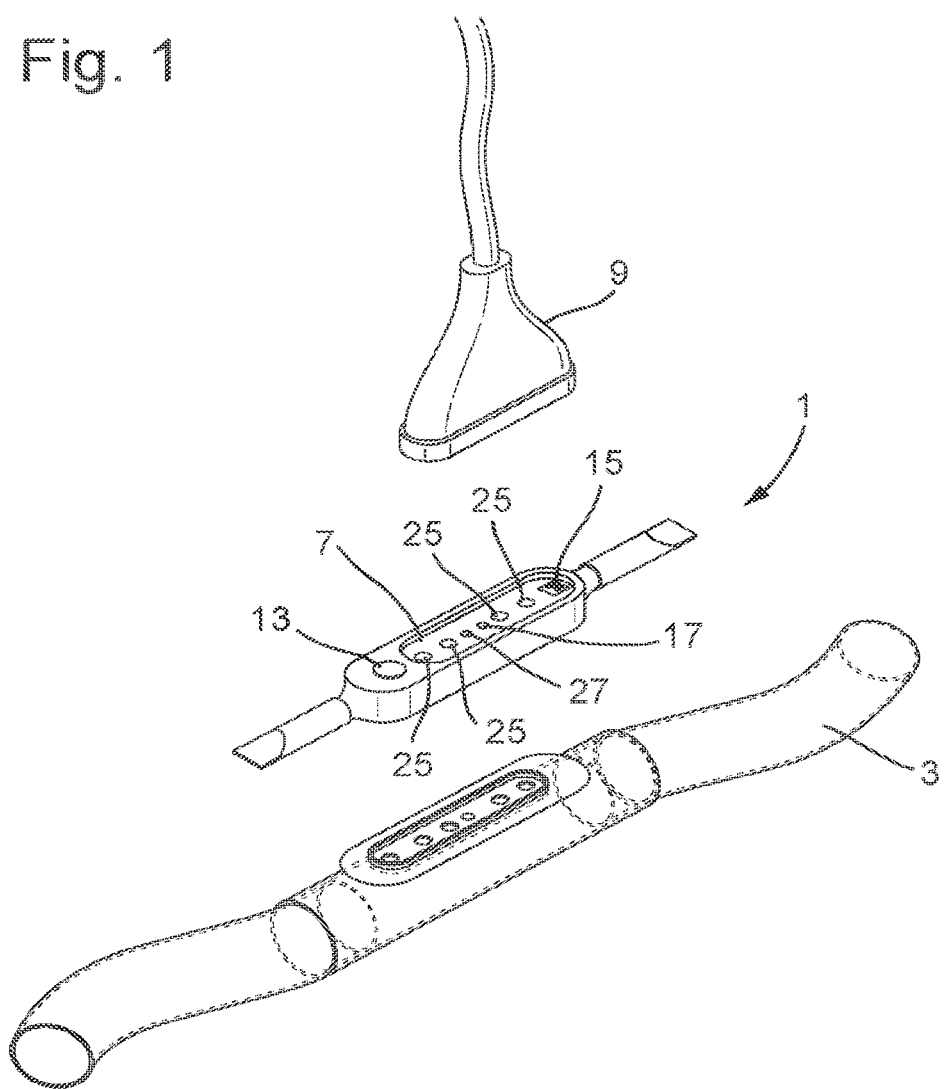
FIG. 1 is an isometric view of a sensor component prior to connection to the one or more waveguides and engagement with the fluid line.

FIG. 1 shows a sensor component 1 for use in a system for measuring the concentration of one or more analytes in fluid in a fluid line 3. The system is preferably a system for use in clinical contexts, for example being part of ECMO, CPB, or CRRT machines as mentioned above. In such cases, the fluid in the fluid line 3 is blood of a patient. However, this is not essential, and the sensor component 1 may also be used in other contexts, for example monitoring of analyte concentrations in gases. Analytes measured by the system using the sensor component 1 may include oxygen, carbon dioxide, hydrogen ions (i.e. pH), potassium, sodium, calcium, magnesium, ammonia, nitric oxide, or anaesthetic gases.

The sensor component 1 comprises a black plastic construction. Plastic can be readily manufactured to the desired specifications and can also be sterilised for use in clinical contexts. However, the use of plastic is not essential, and other suitable materials, for example resin or metal, may be used. The black colour of the sensor component 1 aids in eliminating optical crosstalk between sensing elements 5. However, in general the sensor component 1 may have any colour. Preferably, when used in blood contacting medical devices, the material of the sensor component 1 is biocompatible and non-leaching to prevent contamination of a patient's blood. When used for continuous monitoring application, consideration should also be given to potential inadvertent changes to the properties of the sensor component 1 (in particular the sensing elements 5 and optical parts) post manufacture during shelf life, particularly if the eventual calibration prior to use depends upon constants determined during manufacture. Therefore, materials with chemical and optical properties that are stable over time are preferred. Care should also be taken to ensure that extraneous materials generated during manufacture or sterilization do not negatively impact the drift of the sensor measurements during use and resulting in inaccuracies.

The sensor component 1 is preferably provided to the user packaged so as to be sterile and hydrated with a buffer/calibration solution that has a known or predetermined concentration of the analytes that are to be detected. In the case of some analytes (such as any of the exemplary analytes mentioned above except for hydrogen ions/pH) the predetermined concentration may preferably be zero in some embodiments. When oxygen and/or carbon dioxide are to be detected, their concentrations can be brought to zero by virtue of scavenger materials enclosed in the packaging with the sensor component 1. The buffer/calibration solution provides the first of two calibration points. In some embodiments, the hydration and sterility of the blood contacting surface of the sensor component 1 is maintained by an aluminium removable tab.

The sensor component 1 comprises one or more sensing elements 5. The sensor components shown herein comprise four sensing elements, but this is not essential, and other embodiments may comprise one, two, three, or more than four sensing elements 5. The sensing elements 5 each comprise a luminescent compound, preferably a fluorescent compound, more preferably a fluorescent organic dye. The luminescent compound may be different for different sensing elements 5 and will depend on the analytes to be measured. Examples of suitable luminescent compounds include seminaphtharhodafluor (SNARF), mag-fluo-4, and derivatives thereof. The sensing element may comprise the luminescent compound suspended in, dissolved in, or molecularly bonded to a matrix. The matrix may comprise a polymer, for example PMMA or polystyrene. Alternatively, the matrix may comprise a sol-gel or hydrogel.

Fluorescent optical continuous monitoring sensors may suffer from the photobleaching of the fluorophore of the fluorescent compound, resulting in an effective loss in the concentration of the fluorescent compound in the sensing element 5. This can introduce drift in measurements over time. Photobleaching is typically the result of a portion of the fluorophore molecules being excited to a reactive triplet state, which can then react with materials in the local environment to generate non-fluorescent molecules. The fluorescent compounds are preferably chosen to be robust so as to minimize photobleaching of the fluorophores. Another method to minimise photobleaching is to optimise the intensity of light used to stimulate the luminescent compounds and optimise the work cycle of the incident exciting light. For instance, if a data point is required every 15 seconds to produce a continuous trend of analyte concentration, then the light source may be "turned on" for just 10 milliseconds every 15 seconds, so is only on for 0.07% of the time. In the example of a 4-hour CPB, the fluorophore is only excited for a total of 10 seconds.

The sensing element 5 has an optical property that varies with the concentration of the one or more analytes in the fluid. The optical property may be emission or absorption of light. In the case where the sensing element 5 comprises a luminescent compound, the optical property may be a luminescence lifetime. The optical property may be the same for all of the sensing elements 5 or may differ between sensing elements 5. Various measurement modalities may be used to minimize drift in sensors. Fluorescent lifetime and ratiometric modalities are commonly used when available, as these are less vulnerable to common sources of error that can cause drift. Ratiometric modalities take two measurements of light from the luminescent compound, for example at different wavelengths, and calculate a ratio. However, often straight intensity measurements methods are the only modalities available, and therefore it is important that aspects of the design of the sensor component 1 are chosen to minimize drift and inaccuracies.

Figure 2:
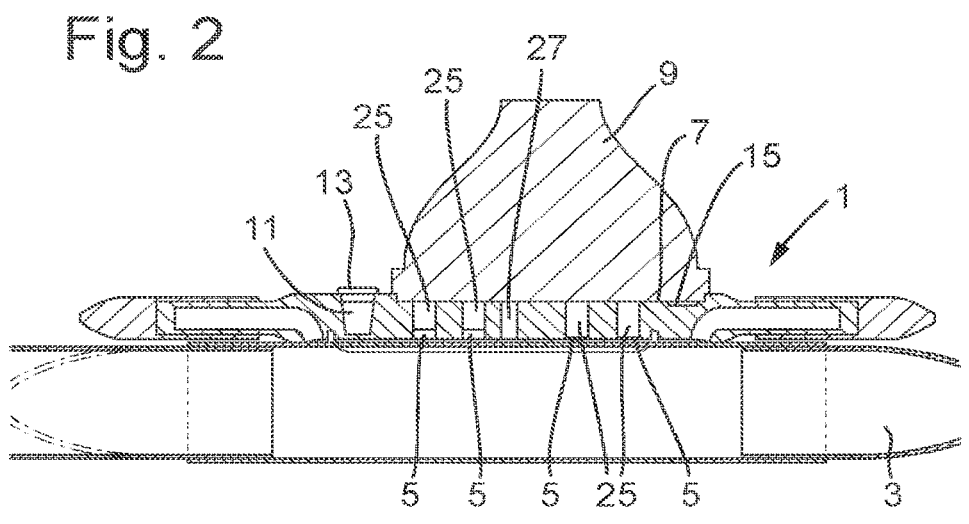
FIG. 2 is a cross-sectional view of the sensor component of FIG. 1 engaged with the fluid line and connected to the one or more waveguides.

The sensor component 1 is configured to engage with the fluid line 3 such that the sensing elements 5 are exposed to the fluid in the fluid line 3. As shown in FIG. 2, the sensor component 1 engages with the fluid line 3 with the sensing element 5 exposed to the interior of the fluid line 3 such that fluid flowing through the fluid line 3 past the sensor component 1 will come into contact with the parts of the sensor component 1 facing the interior of the fluid line 3.

Figure 3:
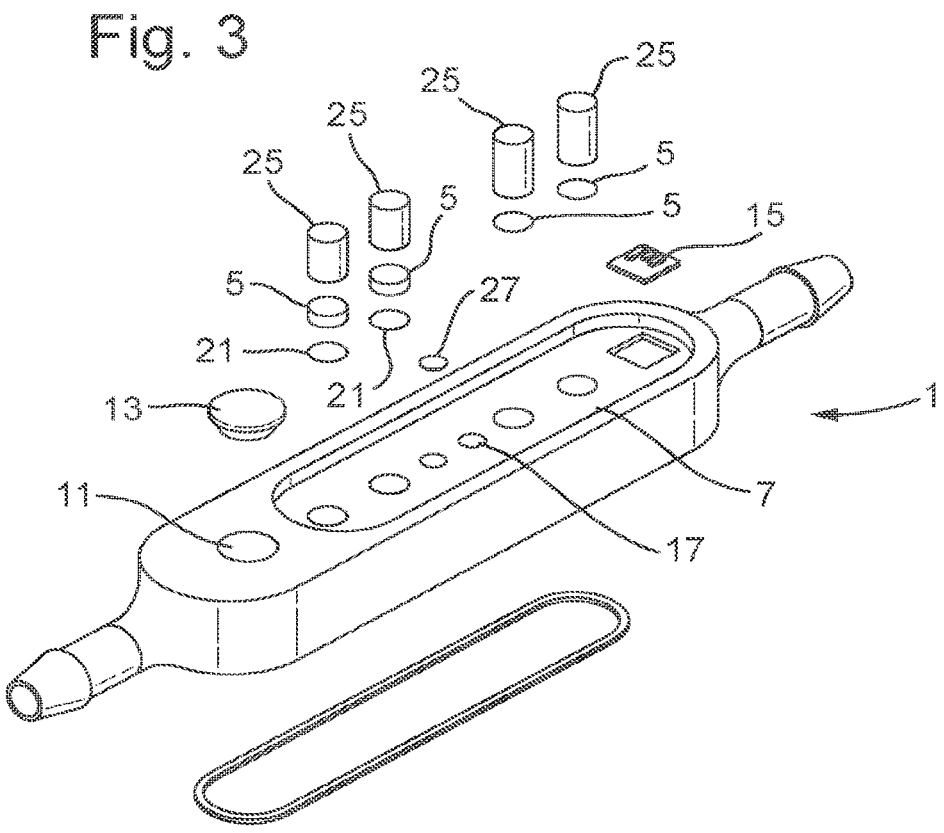
FIG. 3 is an exploded isometric view of the sensor component of FIGS. 1 and 2.

As shown in FIG. 3, two of the sensing elements 5 comprise a membrane 21 permeable to at least one of the analytes configured to be exposed to the fluid in the fluid line 3 when the sensor component 1 is engaged with the fluid line 3. Membranes 21 may in general be provided in respect of any or all of the sensing elements 5. The membrane 21 is permeable to at least the analyte sensed by the sensing element 5 in respect of which the membrane 21 is provided. The provision of a membrane 21 can ensure greater specificity by ensuring that the sensing element 5 is not affected by interaction with analytes other than the one it is intended to sense and preventing interaction of the sensing element 5 with other components of the fluid that may affect the optical property of the sensing element 5. For example, the membrane 21 may prevent large, biological molecules such as proteins, or blood cells from interacting with the sensing elements 5. The membrane 21 may be a hydrophobic gas permeable membrane if the analyte is $O_2$, $CO_2$, $NO$, $NH_3$, or anaesthetic gases. If the analyte is soluble in water or blood plasma, the membrane 21 may be a hydrophilic membrane, for example a hydrogel. Suitable membranes may include microporous or dialysis membranes.

Figure 4:
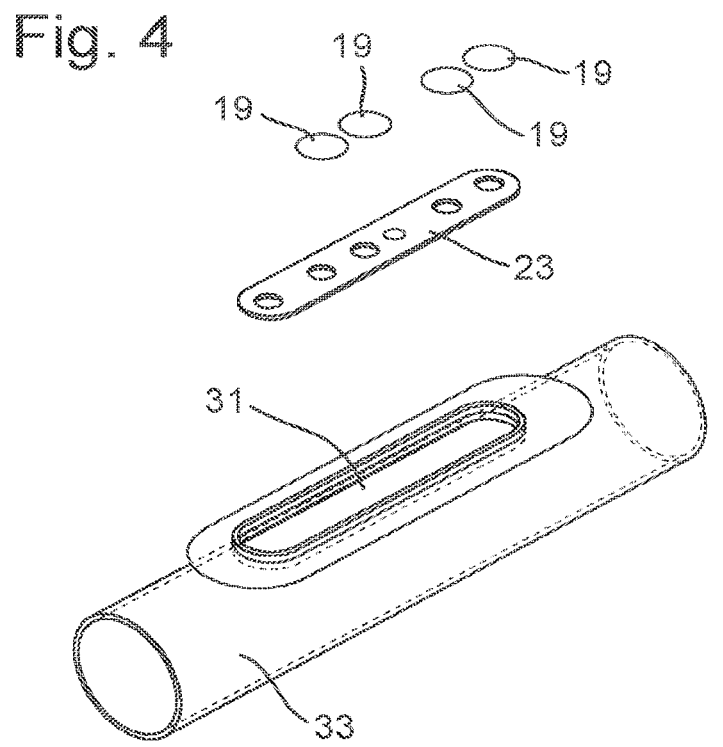
FIG. 4 is an exploded view showing further elements of a sensor component.

As shown in FIG. 4, the sensor component 1 comprises a fluid-permeable support element 19 for supporting the sensing elements 5 arranged to be between the sensing elements 5 and the fluid in the fluid line 3 when the sensor component 1 is engaged with the fluid line 3. The fluid-permeable support element 19 provides mechanical support and protection to the sensing elements 5. This can be advantageous where the flow of fluid in the fluid line 3 is highly pulsatile, for example in CPB or ECMO machines, and has significant pressure fluctuations. Without the fluid-permeable support element 19, such fluctuations could cause small movements or deformations of the sensing element 5, changing the optical path length through the sensing element and affect measurements of its optical property and introducing error. The permeable support element 19 preferably comprises a mesh, for example a stainless steel or plastic mesh. Permeable support elements 19 are provided for each sensing element 5 in the figures, but this may not be necessary depending on the mechanical properties of the individual sensing elements 5.

FIG. 4 also shows that the sensor component 1 further comprises a light-absorbing element 23 positioned between the sensing elements 5. This may be provided in any embodiment where the sensor component 1 comprises two or more sensing elements 5. The light-absorbing element 23 prevents optical cross-talk between the sensing element 5 that could introduce errors in measurements of their optical properties.

The sensor component 1 comprises a connector 7 configured to connect to one or more optical waveguides. In the embodiments shown in the figures, the optical waveguides are comprised by an opto-electrical interface 9, and the connector 7 comprises a recess in the sensor component 1 that engages the interface 9. However, in general the connector 7 may take any suitable form and may comprise retention elements such as clips or screws to prevent movement of the one or more optical waveguides relative to the connector 7.

The optical waveguides allow light to be transmitted to and from one or more light sources elsewhere in the system in which the sensor component 1 is used. In the embodiments shown in the figures, light is transmitted along the interface 9 through the optical waveguides from the one or more light sources. Suitable light sources include LEDs or laser diodes. The opto-electrical interface 9 is generally non-disposable and connects the sensor component 1 to the system for measuring analyte concentration, for example a Patient Data Module (PDM). The optical waveguides may comprise optical fibres or optical fibre bundles to transmit the excitation light to the sensing elements 5. Light emitted from (or transmitted through) the sensing elements 5 is also returned via the optical waveguides in the interface 9 to detectors in the PDM that detect the intensity of light from the sensing elements 5. The optical waveguides are butted against the transparent optical elements 25. The interface 9 also provides a means for electrical connection to the temperature sensor 27 and data storage medium 15.

In other embodiments, the sensor component 1 may comprise the one or more optical waveguides and/or the one or more light sources and detectors, and the interface 9 may provide only electrical connection to other parts of the system, or may be entirely absent. The sensor component 1 is configured to transmit light between the one or more optical waveguides and the one or more sensing elements 5, such that the optical property of the sensing elements 5 can be measured.

As shown in FIG. 2, the connector 7 comprises a transparent optical element 25 in respect of the or each sensing element 5 configured to transfer light between the sensing element 5 and the one or more optical waveguides. This provides protection for the sensing elements 5 to prevent physical or chemical damage, particularly when the interface cable 9 is not connected. The transparent optical element 25 may itself comprise a waveguide to ensure optimal transmission of light to and from the sensing elements 5. The transparent optical elements 25 act as optical windows that interface the optical waveguides with the sensing elements 5.

As shown in FIGS. 1 to 3, the sensor component 1 comprises a temperature sensor 27 arranged to sense the temperature of the one or more sensing elements 5. The optical property of the sensing elements 5, and/or its dependence on the concentration of analyte, may vary depending on the temperature of the sensing element 5. Therefore, knowing the temperature of the sensing elements 5 can improve the accuracy of determination of the concentration of analyte in the fluid. Preferably, the temperature-sensitive element 27 is a thermistor or a thermocouple. The sensor component 1 may comprise one or more electrical contacts, or contact wells, to permit electrical connection to the temperature-sensitive element 27 for the purposes of measuring temperature. The temperature sensor 27 may also be used for measuring blood temperature.

There are two main options for placing the sensor component 1 into the fluid line 3, which may be an extracorporeal blood line. The sensor component 1 may be placed into the main fluid line 3 itself, or as a shunt in a line peripheral to the main fluid line 3. The sensor component of FIGS. 1 to 5 is configured to engage with a wall of the fluid line 3. This embodiment is therefore engaged with the main fluid line 3.

In some embodiments, the sensor component 1 further comprises a conduit 29, the sensing elements 5 being exposed to fluid in the conduit 29. The conduit 29 may comprise a section of the same type of tubing as the fluid 3, for example the section of tubing with which the sensor component 1 engages in FIG. 5. The conduit 29 may be configured to be inserted into the fluid line 3 for engagement of the sensor component with the fluid line 3. As mentioned above, the conduit 29 may be configured to be inserted into the fluid line 3 in an in-line configuration, or in a shunt configuration (also referred to as a bypass configuration).

Accurate calibration pre-use is important to achieve subsequent accurate monitoring. Point of use calibration should also be made as simple for the user as possible, if not totally invisible. The sensor component 1 described herein uses a calibration method requiring two calibration measurements at the point of use.

Figure 5:
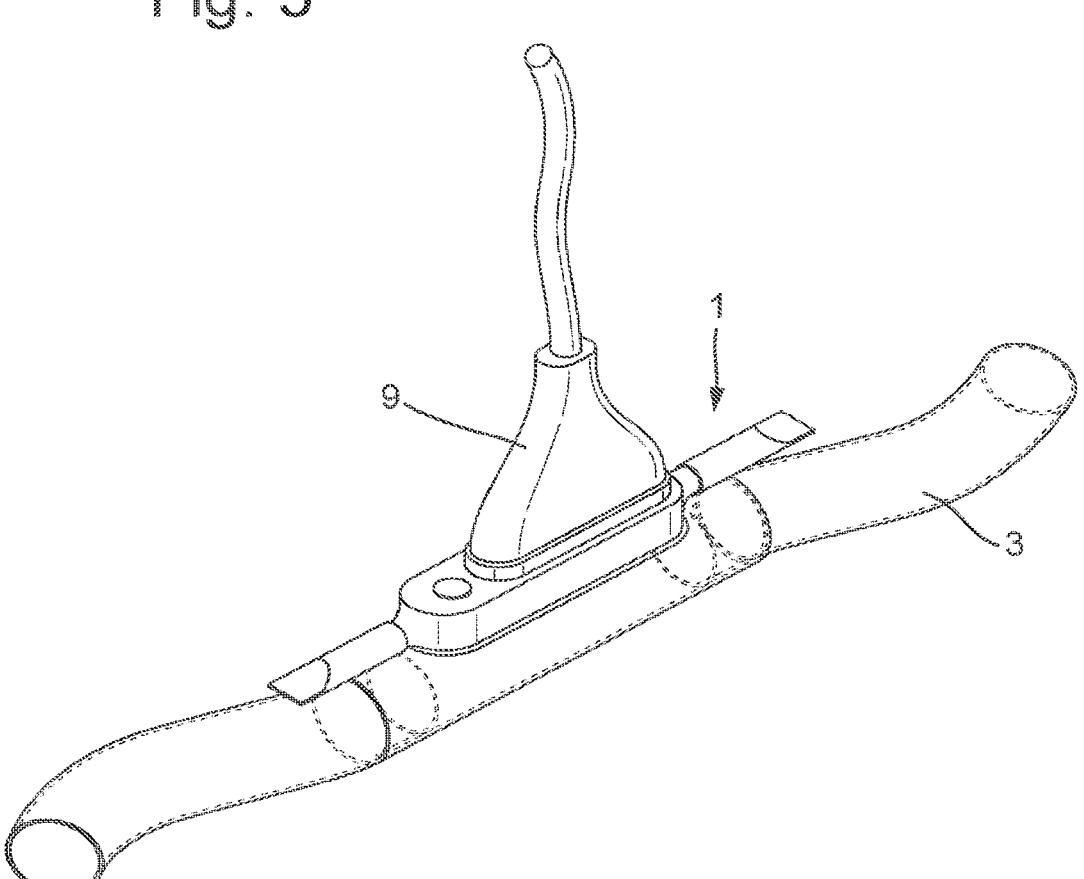
FIG. 5 is an isometric view of the sensor component of FIGS. 1 to 3 engaged with the fluid line.

For an embodiment such as shown in FIG. 5, where the sensor component 1 engages with the main line of the fluid line 3, the setup process for use of the sensor component 1 may be as follows.

Prior to engagement of the sensor component 1 with the fluid line 3, the sensor component 1 is provided hydrated (with the sensing element 5 exposed to a buffered solution) and sterile within a separate pack. The in-line connector 33 with which the sensor component 1 engages is already integrated into the fluid line 3, with a protective cap/plug in place covering the aperture 31. Where the sensor component 1 comprise a conduit 29, the in-line connector 33 may function as the conduit 29. The sensor component 1 is then connected to the interface 9, which provides via the one or more optical waveguides, the transmitted light at an appropriate wavelength for measuring the optical property of the respective sensing elements 5. The one or more optical waveguides also allow for the return of light back to detectors in the system. The buffered solution in the packaging of the sensor component 1 preferably contains a known or predetermined concentration of the analytes to be measured.

The system automatically measures a first calibration point for the one or more analytes when the sensor component 1 is connected to the interface, this process being invisible to the user, thereby improving ease of use. The hydration/buffer solution, which may be trapped behind an aluminium foil layer, acts as a first calibration solution.

The in-line connector 33 is filled with a priming fluid, which may have known concentrations of the one or more analytes different to the concentration in the buffered solution. The protective cap/plug is removed from the aperture 31 at the same time as a protective covering is removed from the sensing element 5, and the sensor component 1 is immediately attached to the in-line connector 33. The priming fluid is displaced by the fluid (e.g. blood).

Once the sensor component 1 is placed in-line and the sensing elements 5 are in contact with the fluid, a fluid sample is taken adjacent to the sensor component 1 either upstream or downstream in the fluid line 3. The concentration of the one or more analytes in the sample are measured on an approved external analyser such as a blood-gas analyser. The data are fed back into the system to provide a second calibration point.

Figure 6:
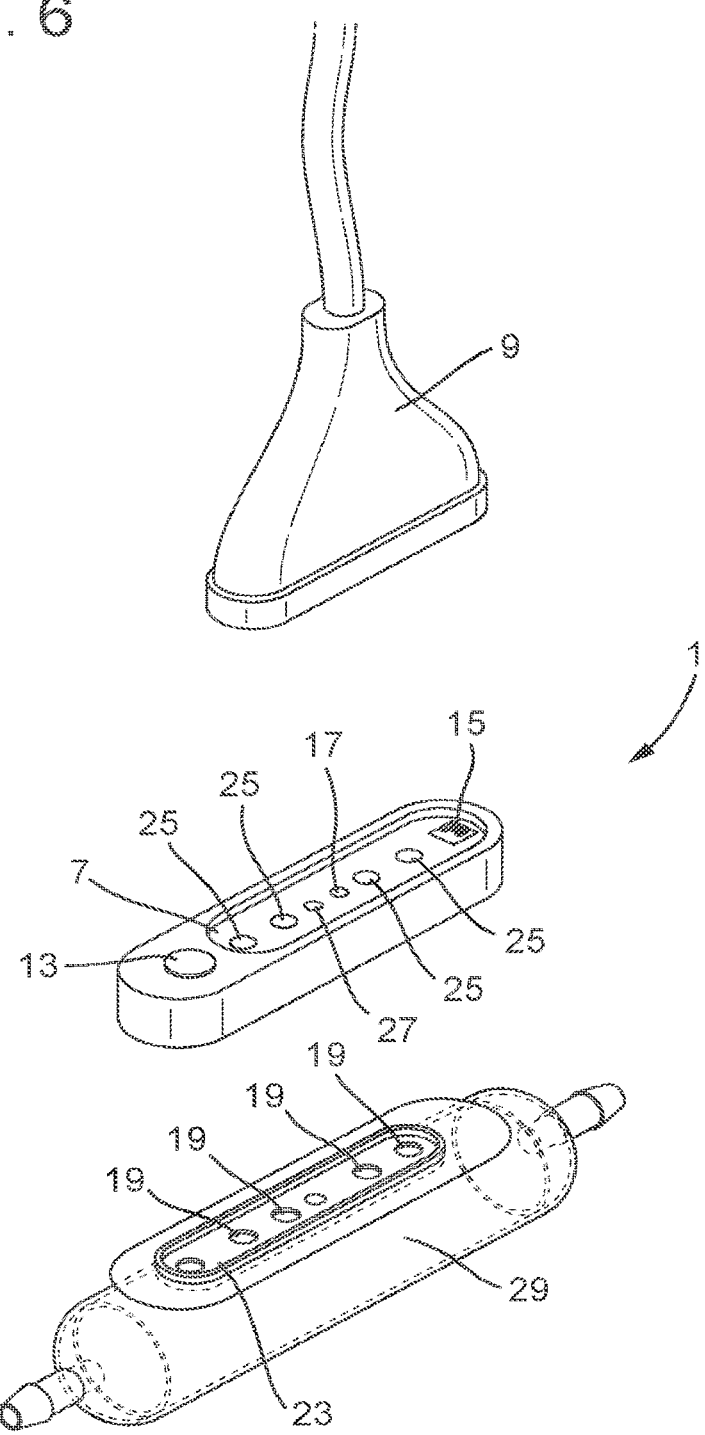
FIG. 6 shows an embodiment of a sensor component comprising a conduit.

An alternative to the sensor component 1 engaging with the main line of the fluid line 3 as just described is a shunt system that by-passes the mainline. In such embodiment, the sensor component 1 comprises a conduit 29, as shown in FIG. 6, integrated into one sterile device. The conduit 29 is then configured to be inserted into the fluid line 3 in a shunt configuration, also referred to as a shunt configuration. The conduit 29 may be joined to the rest of the sensor component 1 by any suitable means, for example by ultrasound welding.

For an embodiment such as shown in FIG. 6, where the sensor component 1 engages with the fluid line 3 in a shunt configuration, the setup process for use of the sensor component 1 may be as follows.

As for the in-line configuration described above, the sensor component 1 is provided hydrated and sterile within a separate pack. However, in this embodiment, the sensor component 1 also comprises the conduit 29. The sensor component is packaged with attached shunt tubing 35 and shunt taps 37 which are also sterile. The main fluid line 3 is provided with taps 39 to receive the shunt tubing 35. The main fluid line 3 will be sterilised with the extracorporeal tubing set. As for the in-line configuration, the sensor component 1 is connected to the interface 9 to measure a first calibration point.

Protective caps are then removed from the shunt taps 37, and the shunt taps 37 connected to the taps 39 in the main fluid line. The shunt taps 37 are then opened, and fluid flows through the shunt tubing and through the conduit 29. The sensing elements 5 are exposed to the fluid in the conduit 29. Finally, as for the in-line configuration, a sample of fluid is taken and used to provide a second calibration point.

A large number of factors can influence the accuracy and drift in measurements of the optical property of the sensing elements 5. Where the sensing elements 5 comprise a fluorescent compound, fluorescence emission $F_1$ is given by $$F_1 = I_0(2.303\varepsilon cl)\varphi$$

where:

$I_0$ is the intensity of light entering the sensing element 5. This light originates from the one or more light sources and is transmitted to the sensing elements 5 via the one or more optical waveguides;

$\varepsilon$ is the absorptivity or molar attenuation coefficient and is constant for a given fluorescent compound. It is defined as the light absorbed by a 1 molar concentration of the detecting fluorescent compound with a path length of 1 cm;

c is the concentration of the absorbing species, which in this example is the fluorescent compound;

l is the optical path length between the light source and detector which contains the fluorescent compound;

$\varphi$ is the quantum efficiency and is a measure of a change of energy when a molecule is excited to a high energy level and then drops to a lower energy with the emission of fluorescence.

All of these parameters are accounted for and kept constant during the process of calibration. Changes in their values post calibration, either continuously or suddenly by damage to the sensor component 1, will result in inaccuracy in the measurements of analyte concentration either through gradual drift or a more sudden change in signal. The design of continuous sensor components should keep these parameters constant as far as possible. It is likely that only low-level drift will be encountered after all of the means of reducing drift have been applied to the sensor component 1 design. Therefore inaccuracies will only become significant over long periods of time. This is unlikely to be a problem for CPD, but is possible for lengthy dialysis and ECMO treatment.

As discussed above, to provide a second calibration point, a sample of fluid is required. The first aspect of the invention concerns a sampling port 11 as shown in FIGS. 2 and 3. The sampling port 11 is configured to provide fluidic access to the fluid line 3 when the sensor component 1 is engaged with the fluid line 3, as shown in FIG. 2.

The provision of the sampling port 11 integrated into the sensor component 1 ensures that the fluid sample is taken from the fluid flowing over the sensing elements 5 close to or as near as possible to the sensing elements 5, to ensure accuracy of calibration. In some embodiments, the sampling port 11 is at most 20 cm, preferably at most 10 cm, more preferably at most 5 cm from the one or more sensing elements 5.

Proximity of the sampling port 11 to the sensing elements 5 is advantageous because a fluid sample taken distant from the sensing elements 5 may have analyte concentrations different from those measured by the sensing elements 5 at the time the fluid sample is taken. For example, this can occur due to metabolism of the analyte. This will mean the concentration in the fluid sample is not representative of the concentration measured by the sensing elements 5, causing a calibration error and subsequent measurement errors. Samples may be taken through the sampling port 11 in any suitable manner, for example using a syringe.

The sampling port 11 comprises a one-way valve configured to permit one-way fluid flow out of the fluid line 3. This allows fluid samples to be taken without compromising sterility of the fluid line 3 or risking any contamination of the fluid in the fluid line 3. The sampling port 11 comprises a component fitting configured to engage with an external fitting. This allows for a secure connection when taking samples. Specifically, the component fitting comprises a Luer fitting, such that the sampling port 11 is a Luer-activated sampling port. While a Luer fitting is preferred, it is not essential, and other suitable types of component fitting may also be used.

The sampling port 11 is configured to open upon engagement of the external fitting with the component fitting. The sampling port 11 may further be self-closing. This helps to improve ease of use for the user, and to assure sterility and eliminate leaks of fluid from the fluid line 3 through the sampling port 11. The sampling port 11 further comprises a removable cap 13 configured to seal the sampling port 11, although this is not essential. The removable cap 13 can protect the sampling port 11 from damage or contamination if it is not used for extended periods of time.

The second aspect of the invention concerns a data storage medium 15 configured to store data representing information about the sensor component 1. This is particularly useful where the sensor component 1 is replaceable. For example, where the sensor component 1 is designed to be disposable and intended for use only in a single treatment for a single patient. The data storage medium 15 may comprise a microchip.

To enable the above-mentioned method of calibration that requires only two calibration points at the point of use, some of the properties of the sensing elements 5 and the sensor component 1 may be determined during or after manufacture, before the replaceable sensor component 1 is supplied to the end user. These properties travel with the replaceable sensor component 1 stored by memory in the data storage medium 15. This is particularly useful, for example, if the detection characteristics of the sensor component 1 vary between manufacturing batches. The data storage medium 15 may also store data to ensure that the replaceable sensor component 1 is in good working order at the time of calibration and use, and/or data to ensure compliance with various legal and/or clinical requirements on the replaceable sensor component 1 and its use.

In some embodiments, the sensor component 1 may comprise an interface circuit configured to transmit signals between the data storage medium 15 and the system. This allows for data to be accessed from and written to the data storage medium 15. The interface circuit may provide for optical and/or electrical transmission of signals to and from the data storage medium 15. It may alternatively be configured to transmit the signals wirelessly, in which case the interface circuit may comprise an antenna. In some embodiments, the data storage medium 15 may comprise the interface circuit. In other embodiments, the data storage medium may not require an interface circuit for data stored to be accessed or modified, and may merely comprise electrical contacts for an external connection, for example via the interface 9.

The data storage medium 15 may be read-only in respect of some or all of the information stored by the data storage medium 15. For example the information determined at the time of manufacture may not be modifiable by the end user. Other types of information may be modifiable or settable by the end user. The data storage medium 15 may be configured such that some or all of the information can be set only once by the end user and is not subsequently modifiable.

The information comprises one or more characteristics of the one or more sensing elements 5. In particular, the information may comprise calibration information about the variation of the optical property of the sensing elements 5 with one or both of the concentration of the one or more analytes and the temperature of the sensing elements 5.

The information may further comprise one or more characteristics of a calibration fluid used for calibration of the replaceable sensor component 1. The calibration fluid may comprise the buffer solution mentioned above. For example, the information may comprise a variation of the pH of the calibration fluid with temperature. This will improve the accuracy with which the calibration can be determined from the two calibration points.

The information may also comprise information concerning the use of the replaceable sensor component 1. For example, the information may comprise an identifier of a patient with whom the replaceable sensor component 1 is associated. This information may be used to prevent reuse of the sensor component 1. The data storage medium 15 may be configured to receive the identifier during initialisation of the system and store the identifier such that the replaceable sensor component 1 is permanently associated with the patient. As mentioned above, this may be achieved by allowing the information regarding the patient identifier to be set only once in the data storage medium 15. Similarly, the information may comprise an identifier of the system with which the replaceable sensor component 1 is associated. This can be used to prevent reuse of the sensor component 1. Storing an identifier of the system can also reduce inaccuracies in the determined concentrations of the analytes, as the properties of the light sources and detectors used to measure the optical property of the sensing elements 5 may vary between systems. As for the patient identifier, the system identifier may also be set permanently during initialisation of the system.

Other information that may be stored by the data storage medium 15 may include:

an indication of prior use of the replaceable sensor component 1;

an indication of whether damage has occurred to the replaceable sensor component 1;

a use-by date after which the replaceable sensor component 1 should not be used;

an in-use lifetime of the replaceable sensor component 1, i.e. a maximum length of time for which the sensor component 1 should be used, for example 128 hours;

a length of time for which the replaceable sensor component has been used;

a unique identifier of the replaceable sensor component;

a date of manufacture of the replaceable sensor component;

a time at which the replaceable sensor component was last calibrated; and an indication of the number and/or type of errors that have occurred during use of the replaceable sensor component.

Figure 7:
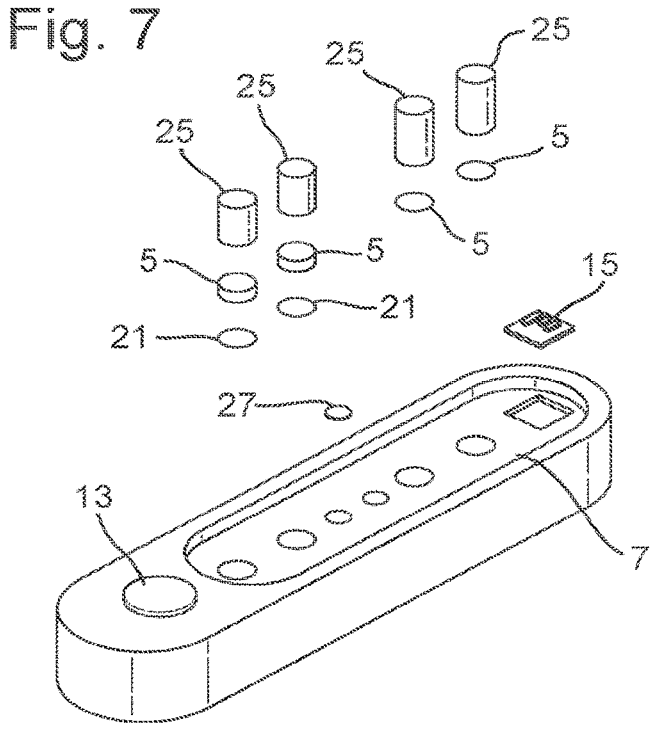
FIG. 7 shows an exploded view of part of the sensor component of FIG. 6.
Figure 8:
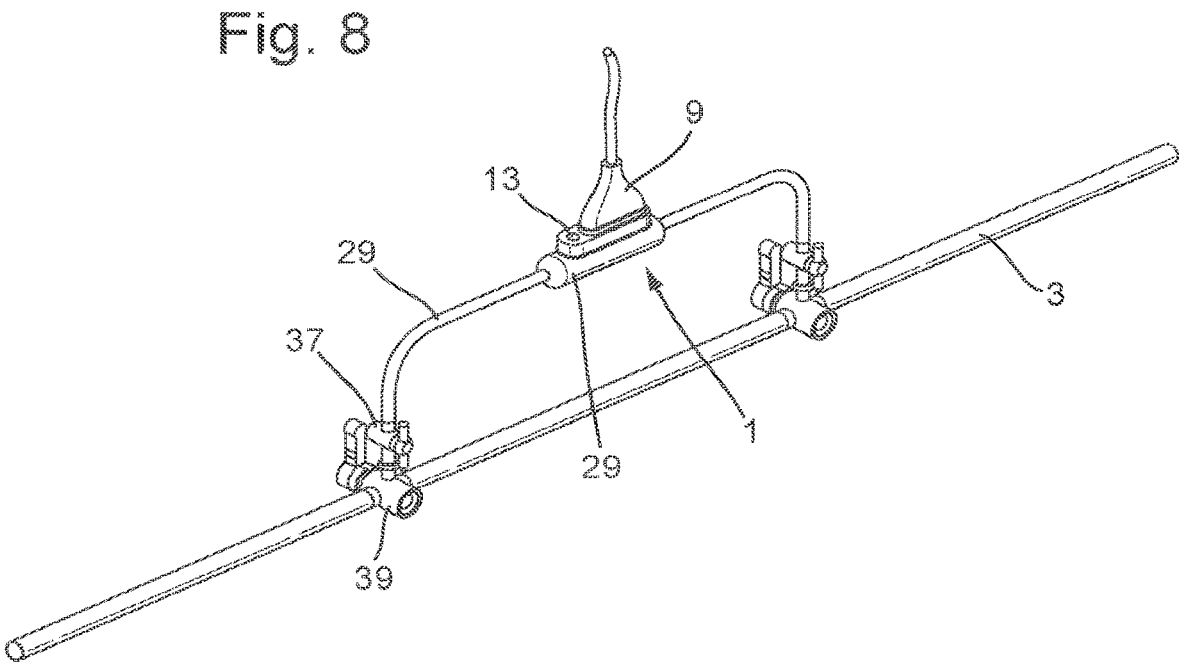
FIG. 8 shows the sensor component of FIG. 6 engaged with the fluid line in a shunt configuration.

The third aspect of the invention concerns a reflective element 17 as shown in FIGS. 3 and 7. As mentioned above, one of the parameters which may affect the measurements of the optical property of the sensing elements 5 is the optical path length between the light source in the system and the detector that detects the light after it has passed through the sensing element 5. This optical path length may be affected by small mechanical shifts of the optical interfaces, for example between the optical waveguides and the sensing elements. It may also be affected by damage to one or more of the optical waveguides.

To reduce the adverse effect of such errors, the sensor component 1 comprises a reflective element 17. The sensor component 1 is configured also to transmit the light between the one or more optical waveguides and the reflective element 17 on a separate optical path from an optical path between the one or more optical waveguides and the one or more sensing elements 5. This provides a reference beam, generating a reference signal at the detector, against which the light transmitted between the optical waveguides and the one or more sensing elements 5 can be compared. The reflective element may be, for example, a reflecting mirror.

The optical path between the one or more optical waveguides and the reflective element 17 is preferably a replicate of the optical paths between the one or more optical waveguides and the sensing elements 5, with the exception that the optical path between the one or more optical waveguides and the reflective element 17 does not pass through a sensing element 5. The light reflected by the reflective element 17 is therefore not altered by analyte concentration. This means that a ratio can be calculated between the signals obtained from the sensing elements 5 and the reference signal during calibration and during continuous measurements. Thereby, a measurement is obtained in which the optical path length in the equation above is cancelled out, and the use of the ratio ensures that any inaccuracies generated by small mechanical shifts in optical interfaces do not affect the measurement. Further, if the same light source is used for measuring the optical property of the sensing element 5 as is used for the reference beam, the initial intensity $I_0$ is also cancelled out in the equation above, and so the generation of light losses through minor damage to optical fibres (which causes a change of $I_0$) will also not affect the measurement.

The reference beam must be distinguishable from the light which has passed through the one or more sensing elements 5 in order that the ratio can be calculated. The reference beam may be optically distinguishable, e.g. by having a different wavelength to the light passing through the sensing elements, and/or may be physically distinguished by travelling along a separate optical path between the light source, the reflective element 17, and the detector from the optical path between the light source, sensing elements 5 and detector. Therefore, if the same light source is used for measuring the optical property of the sensing element 5 as is used for the reference beam, the reference beam must be physically distinguished from the light that passes through the sensing element 5.

The use of a ratio can normally only accommodate minor damage or shifts to optical interfaces post-calibration while still allowing the sensor component 1 to operate normally. Catastrophic damage will result in a sudden change in signal (in either or both of the reference signal or the signal from the sensing elements 5) which will be recognized by the system as not being due to a physiological change. In this case, the system will generate a warning to alert the user that the data is suspect and should be received with caution.

It is not essential that the optical path between the one or more optical waveguides and the reflective element 17 is the same as the optical paths between the one or more optical waveguides and the sensing elements 5 to obtain an advantage. For example, where the same light source is used for measuring the optical property of the sensing element 5 as is used for the reference beam, a ratio of the reference signal and the signal from the sensing elements 5 can still reduce the effect of changes in the initial intensity $I_0$. In addition, for a sensor component 1 with multiple sensing elements 5, the presence of the reference beam makes it possible to distinguish where a sudden large change in signal from a sensing element 5 is due to failure of the sensing element 5 or from other causes.

In the embodiments shown in the figures, the reflective element 17 is concave, i.e. a concave reflector. This is preferred to improve the collection of light reflected by the reflective element 17. However, it is not essential, and in other embodiments, the reflective element 17 may be planar.

The amount of light (i.e. as a proportion of the amount of light incident on the reflective element 17) reflected by the reflective element 17 is not important to the function of the reflective element 17, as long as the proportion reflected is consistent over time. However, reflection of a larger proportion of the incident light improves signal to noise at the detector, and makes the effect of noise on the ratio measurement less significant. Therefore, it is preferable that the reflective element 17 is configured to reflect at least 10%, preferably at least 25%, more preferably at least 50%, of light incident thereon back to the one or more waveguides.

The invention claimed is:

1. A sensor component for use in a system for measuring the concentration of one or more analytes in fluid in a fluid line, the sensor component comprising:

one or more sensing elements having an optical property that varies with the concentration of the one or more analytes in the fluid, the sensor component being configured to engage with the fluid line such that the sensing elements are exposed to the fluid in the fluid line when the sensor component is engaged with the fluid line;

a connector configured to connect to one or more optical waveguides, the sensor component being configured to transmit light between the one or more optical waveguides and the one or more sensing elements;

a reflective element, wherein:

the sensor component is configured to transmit the light between the one or more optical waveguides and the reflective element;

the reflective element is configured to reflect at least 10% of light incident thereon back to the one or more waveguides; and the light transmitted by the sensor component between the one or more optical waveguides and the reflective element has a different wavelength to the light transmitted between the one or more optical waveguides and the one or more sensing elements.

2. A sensor component according to claim 1, wherein the reflective element is concave.

3. A sensor component according to claim 1, wherein the reflective element is planar.

4. A sensor component according to claim 1, further comprising a fluid-permeable support element for supporting the sensing elements arranged to be between the sensing elements and the fluid in the fluid line when the sensor component is engaged with the fluid line.

5. A sensor component according to claim 4, wherein the permeable support element comprises a mesh.

6. A sensor component according to claim 1, wherein the sensing elements comprise a membrane permeable to at least one of the analytes configured to be exposed to the fluid in the fluid line when the sensor component is engaged with the fluid line.

7. A sensor component according to claim 1, wherein the sensor component comprises two or more sensing elements.

8. A sensor component according to claim 7, further comprising a light-absorbing element positioned between the sensing elements.

9. A sensor component according to claim 1, wherein the connector comprises a transparent optical element in respect of the or each sensing element configured to transfer light between the sensing element and the one or more optical waveguides.

10. A sensor component according to claim 9, wherein the transparent optical element comprises a waveguide.

11. A sensor component according to claim 1, further comprising a temperature sensor arranged to sense the temperature of the one or more sensing elements.

12. A sensor component according to claim 11, wherein the temperature sensor comprises a thermistor or a thermocouple.

13. A sensor component according to claim 1, wherein the sensor component is configured to engage with a wall of the fluid line.

14. A sensor component according to claim 1, wherein the sensor component further comprises a conduit, the sensing elements being exposed to fluid in the conduit and the conduit is configured to be inserted into the fluid line for engagement of the sensor component with the fluid line.

15. A sensor component according to claim 14, wherein the conduit is configured to be inserted into the fluid line in an in-line configuration.

16. A sensor component according to claim 14, wherein the conduit is configured to be inserted into the fluid line in a shunt configuration.

17. A sensor component according to claim 1, wherein the sensor component is configured to transmit the light between the one or more optical waveguides and the reflective element on a separate optical path from an optical path between the one or more optical waveguides and the one or more sensing elements.

\* \* \* \* \*